US008497678B2

(12) United States Patent
Rudakov

(10) Patent No.: US 8,497,678 B2
(45) Date of Patent: Jul. 30, 2013

(54) METHOD AND APPARATUS USABLE FOR MINING AND MINERAL EXPLORATION

(75) Inventor: Taras Rudakov, West Perth (AU)

(73) Assignee: LynxRail Corporation, Colorado Springs, CO (US)

( * ) Notice: Subject to any disclaimer, the term of this patent is extended or adjusted under 35 U.S.C. 154(b) by 420 days.

(21) Appl. No.: 12/842,285

(22) Filed: Jul. 23, 2010

(65) Prior Publication Data

US 2011/0018535 A1 Jan. 27, 2011

Related U.S. Application Data

(60) Provisional application No. 61/228,798, filed on Jul. 27, 2009.

(51) Int. Cl.
*G01V 3/00* (2006.01)

(52) U.S. Cl.
USPC .......................................... 324/303

(58) Field of Classification Search
USPC .................................. 324/300–322
See application file for complete search history.

(56) References Cited

U.S. PATENT DOCUMENTS

| | | | | |
|---|---|---|---|---|
| 3,858,111 | A * | 12/1974 | Simpson, Jr. | 324/310 |
| 4,742,304 | A | 5/1988 | Schnall et al. | |
| RE33,259 | E | 7/1990 | Crooks et al. | |
| 4,994,746 | A * | 2/1991 | Panosh | 324/322 |
| 5,162,734 | A * | 11/1992 | Rapoport | 324/307 |
| 5,166,620 | A * | 11/1992 | Panosh | 324/322 |
| 5,194,809 | A | 3/1993 | Lew | |
| 5,592,086 | A * | 1/1997 | Weinstock et al. | 324/318 |
| 6,617,169 | B2 * | 9/2003 | Ke et al. | 436/173 |
| 6,856,132 | B2 | 2/2005 | Appel et al. | |
| 6,911,822 | B2 * | 6/2005 | Augustine et al. | 324/324 |
| 7,009,394 | B2 * | 3/2006 | Ross | 324/307 |
| 7,012,427 | B2 * | 3/2006 | Augustine et al. | 324/307 |
| 7,109,714 | B2 | 9/2006 | Rudakov et al. | |
| 7,339,377 | B2 * | 3/2008 | Augustine et al. | 324/321 |
| 8,093,056 | B2 * | 1/2012 | Ganesan | 436/28 |
| 2003/0030436 | A1 | 2/2003 | Hennig et al. | |

(Continued)

FOREIGN PATENT DOCUMENTS

| | | |
|---|---|---|
| WO | WO 2008/034867 | 3/2008 |
| WO | WO 2009/089007 | 7/2009 |

OTHER PUBLICATIONS

International Search Report and Written Opinion for International Appln. No. PCT/US10/04327 dated Sep. 16, 2010.

*Primary Examiner* — Dixomara Vargas
(74) *Attorney, Agent, or Firm* — Boardman & Clark LLP

(57) ABSTRACT

A method for mineral analysis of a sample based on detection of NQR and/or Local Field Magnetic Resonance (LFMR) signals from a particular substance within a sample includes: setting a frequency of RF pulses to be approximately equal to one of the NQR or LFMR frequencies of the substance; setting a set of parameters of the RF pulses to be optimal for the substance; setting a set of receiving parameters to be optimal for the substance; tuning the probe to maximum sensitivity for the signals detected at predetermined frequency and/or to maximum power transfer efficiency for RF pulses transmitted with the probe; transmitting the RF pulses with the probe at said optimal level during a transmitting period to irradiate the sample and excite an NQR or LFMR signal in the substance, if present; detecting and processing NQR or LFMR signals emitted by the substance; and calculating the concentration of the substance in the sample.

10 Claims, 5 Drawing Sheets

U.S. PATENT DOCUMENTS

| | | | |
|---|---|---|---|
| 2004/0090230 A1 | 5/2004 | Appel et al. | |
| 2004/0210289 A1* | 10/2004 | Wang et al. | 607/116 |
| 2004/0254419 A1* | 12/2004 | Wang et al. | 600/8 |
| 2005/0025797 A1* | 2/2005 | Wang et al. | 424/422 |
| 2005/0079132 A1* | 4/2005 | Wang et al. | 424/1.11 |
| 2005/0107870 A1* | 5/2005 | Wang et al. | 623/1.44 |
| 2007/0010702 A1* | 1/2007 | Wang et al. | 600/8 |
| 2007/0210798 A1 | 9/2007 | Race et al. | |
| 2009/0121718 A1 | 5/2009 | Yamamoto et al. | |

* cited by examiner

METHOD AND APPARATUS USABLE FOR MINING AND MINERAL EXPLORATION

This application claims priority to U.S. Provisional Application 61/228,798, filed on Jul. 27, 2009, which is incorporated herein by reference in its entirety.

BACKGROUND

1. Field

This invention relates to a method and apparatus for a mineralogy analysis. This invention more particularly relates to a method and apparatus for ore grade estimation.

2. Background

Different active nuclear techniques have been widely used to produce information on the chemical composition of rocks and ore in the laboratory conditions. These techniques include gamma-ray spectrometry, X-ray fluorescence (XRF) and neutron activation. These techniques are not widely used for mining operations (e.g., in blast holes and exploration holes) because, for example, no single nuclear technique is sufficiently useful alone (e.g., none of the known techniques can solve a sufficient number of the common, relevant ore estimation problems).

Known neutron activation (e.g., neutron gamma-ray) methods may be used for measuring a concentration of one or more metals, such as copper, manganese and nickel in ore.

Nuclear Magnetic Resonance (NMR) is widely used as a borehole logging method for the oil and gas exploration. The characterization of hydrocarbon reservoirs in subsurface earth formation is of considerable interest in the oil and gas industry. In this industry, NMR is used for detecting proton resonance in liquids.

SUMMARY

It should be appreciated that the term "substance" as used in the following description, may be taken to mean those desired materials and/or substances which respond in a desired way to NQR and/or NMR phenomenon and techniques.

Many substances that are relevant in detecting explosives contain quadrupolar nuclei, such as, for example, nitrogen-14 (14N) and can be detected using NQR methods. The spectral lines of such substances are located at low frequencies, where detected NQR signals have very low intensity.

However, a number of problems associated with deploying NQR techniques in the field as a reliable and sensitive technique to ascertain the presence of the targeted substance have arisen, limiting the functionality and/or the feasibility of such techniques. For example, low intensity of NQR signals, external interferences and/or spurious signals, which can be detected from surrounding items each, in various ways, may reduce the functionality and/or feasibility of using NQR techniques in the field.

Likewise, direct detection of ore zones by using borehole gamma-ray spectrometry is limited to radioactive minerals. As such, indirect detection (e.g., potassium-enriched sericitic or feldspathic alteration associated with gold mineralization) and characteristics of host rock (e.g., phases of kimberlite) are normally used for these purposes.

Further, XRF methods are not widely used in exploration and mining borehole logging primarily because of the low energies involved and hence the shallow depth of penetration (e.g., limited analysis, if any, beyond a surface analysis) and because the borehole conditions (e.g., surface rugosity) have a large effect on the result. Additionally, the low energies detected often require a relatively thin window over the detector, which may be vulnerable under water-filled borehole conditions.

Furthermore, active nuclear techniques use radioactive sources, which may be unsafe for surrounding humans, animals, plant life and/or equipment. As such, active nuclear systems are predominantly used, if at all, in a borehole-logging configuration, in which the radioactive source is safely contained in the hole during the measurements. It should be appreciated that the radioactive source may be in the form of a radioisotope, an electronic source (e.g., X-ray tubes or neutron generators) and/or any other known or later-developed radioactive source.

Additionally, active nuclear techniques generally cannot directly distinguish between different minerals that contain the same element or elements.

Due, at least in part, to the many difficulties involved with using active nuclear techniques, such techniques are not widely used for mine site exploration and/or ore delineation.

Likewise, the application of conventional NMR methods for mineral analysis is currently very limited. Solid state NMR requires complicated equipment and special detection techniques. Therefore, the method is mostly used in laboratory conditions.

Nuclear Quadrupole Resonance (NQR) techniques have been suggested as being useful in borehole logging methods for minerals bearing such elements as boron, lithium and potassium. Such NQR methods may be preferable over other available methods for any of at least the following reasons: it is a non-radioactive, non-hazardous and/or non-invasive method; it is suitable for the quantitative analysis of solids in place; and/or it is relatively inexpensive and fast.

However, the previously-known detection methods are based on using continuous wave techniques, which may not be efficient, robust and/or sensitive enough to be used for analysis of many desired minerals.

An exemplary method, technique and/or apparatus according to this invention may be particularly useful in mining operations for mine site exploration and/or ore delineation. However, it should be appreciated that various exemplary embodiments of methods, techniques and/or apparatuses according to this invention may be used in other applications, such as, for example assessing mineral content and/or distribution within rock bodies in situ, in soils or sands, in other geological contexts and/or in research.

In various exemplary embodiments of a method and/or an apparatus according to this invention, the method and/or apparatus is usable for mineralogy analysis and/or optimal ore grade estimation for the purpose of mine site exploration and/or ore delineation. In various exemplary embodiments, such methods and/or apparatuses do not exhibit some or all of the disadvantages associated with previous detection methods and systems.

In various exemplary embodiments, a method, apparatus and/or system according to this invention is usable to provide a non-radioactive method with sensitivity and accuracy similar to or better than conventional radioactive nuclear methods.

In various exemplary embodiments, a method according to this invention is usable for distinguishing, differentiating between and/or measuring concentrations of different minerals containing one or more of the same element(s).

In various exemplary embodiments, pure nuclear quadrupole resonance (NQR) and local field magnetic resonance (LFMR) phenomenon and detection techniques are used.

It should be appreciated that both NQR and LFMR techniques are forms of radio frequency (RF) spectroscopy. Likewise, NQR and LFMR are both non-radioactive methods that can be utilized to detect and investigate various chemical compounds. These methods may also be used to detect the presence of specific desired substances, such as, for example, explosives and/or narcotics.

In various exemplary embodiments, NQR methods are used for the analytical detection of chemical substances in solid form. Such NQR methods may provide both elemental composition and mineral phase of bulk material.

Further, in various exemplary embodiments, the NQR methods may be used to characterize many desired compounds (e.g., more than 10,000). Such compounds may include various different elements in the periodic table, which make them desirable. for example, there are a number of nuclei, such as Copper (e.g., 63Cu, 65Cu), Cobalt (e.g., 59Co), Titanium (e.g., 47Ti, 49Ti), Rhenium (e.g., 127Re), Manganese (e.g., 55Mn), Aluminium (e.g., 27Al), Bismuth (e.g., 209Bi), Arsenic (e.g., 75As), Antimony (e.g., 123Sb), indium (e.g., 115I), and Gallium (e.g., 71 Ga) etc., which are important to various industries, and thus may be desirable to identify.

NQR may be defined as a phenomenon of resonance RF absorption and/or emission of electromagnetic energy. NQR phenomena may result, at least in part, due to the dependence of a portion of the energy of electron-nuclear interactions on the mutual orientations of asymmetrically distributed charges of the atomic nucleus and the atomic shell electrons as well as those charges that are outside the atomic radius. Thus, changes in the quadrupole coupling constants and NQR frequencies may be due, at least in part, to their electric origin. The nuclear electric quadrupole moment eQ interacts with the electric field gradient eq, defined by asymmetry parameter $\eta$. Therefore, the nuclear quadrupole coupling constant $e^2Qq$ the asymmetry parameter $\eta$ which helps define structural information about a molecule, may be calculated from the experimental data. The main spectral parameters in the NQR experiments are the transition frequencies of the nucleus and the line width $\Delta f$. Other parameters that may be of interest include, for example, obtaining spin-lattice relaxation time $T_1$, spin-spin relaxation time $T_2$ and line-shape parameter $T^*_2$ (inversely proportional to $\Delta f$). Any of these parameters may affect the choice preferred a preferred experimental technique and/or equipment.

Since the NQR frequencies depend on the molecular structure of these substances they can be used for their practically unique detection and identification.

In contrast to NMR methods, NQR can be performed without a strong external static (DC) magnetic field. This technique may be known as "pure NQR", or direct NQR detection, and may have many advantages over other techniques, at least for some applications. For example, direct NQR may be particularly useful for identification of specific compounds and remote NQR detection. More specifically, these methods may be particularly useful for detecting the presence of specific substances, such as explosives and/or narcotics, as well as landmine detection.

NMR exploits the interaction of nuclei with the magnetic field. Therefore, a strong static field is generally applied to polarize the nuclear magnetic moments. RF fields are used to stimulate the spectroscopic response (NMR signal). A number of minerals (e.g., copper minerals such as, for example, chalcopyrite and cubanite) have a magnetically ordered structure. Thus, NMR can be detected in their local field by means of a NQR technique without applying an external static magnetic field. Therefore, in various exemplary embodiments, both "pure NQR" and/or NMR in local magnetic fields or local field magnetic resonance (LFMR) can be used for mineral analysis and exploration including, for example, borehole logging applications.

Pulsed (including multi-pulse) techniques may be used in NMR and/or NQR spectroscopy. These pulsed techniques may be used, for example, to help increase sensitivity, reduce the experimental time, and/or measure the relaxation time of the sample. In NQR and NMR, single pulses may be used for detection of Free Induction Decay (FID) signals and pulse sequences such as, for example, the spin-echo (SE), Carr-Purcell (CP), Meiboom-Gill-modified CP (CPMG), spin-locking spin-echo (SLSE) sequences and others. Pulse sequences of the steady-state free precession type (SSFP), may be of particular interest. An exemplary one of such sequences is well known in the NQR art as the strong off-resonant comb (SORC).

The probe of a pulsed NQR (or LFMR) detection system is generally a device providing interaction between the radio frequency (RF) field of a resonant RF transmitter and a particular substance that is targeted within a sample for detection of NQR (or LFMR) signals generated as a result of the NQR (or LFMR) phenomena, as well as interaction between the RF field response from the target substance and the receiving part of the NQR (or LFMR) detector. Strong RF pulses, typically with tens or hundreds of watts of power, are used.

In an exemplary embodiment according to this invention, there is provided a method for the mineral analysis of a sample based on detecting NQR and/or NMR signals from a particular substance that is targeted within the sample. In various exemplary embodiments, the method has particular application to (but is not limited to) the fields of mine site exploration and/or ore delineation, such as for example borehole logging of ore formations. In an exemplary embodiment, the method comprises:

(a) setting a frequency of the RF pulses to be approximately equal to one of the nuclear quadrupole resonance or nuclear magnetic resonance frequencies of the desired substance to be analyzed;

(b) setting at least one of the amplitude, phase, duration, shape, number, repetition time and time between pulses of the RF pulses to an optimal level that corresponds to the desired substance to be analyzed;

(c) setting at least one of the gain, reference phase, acquisition time and acquisition number of the receiver to an optimal level that corresponds to the desired substance to be analyzed;

(d) tuning the probe to provide increased sensitivity for the signals detected at predetermined frequency and/or to increase power transfer efficiency for RF pulses transmitted with the probe;

(e) transmitting the RF pulses with the probe during a prescribed transmitting period to irradiate the sample and excite an NQR and/or LFMR signal in the sample if the desired substance is present;

(f) detecting and processing NQR or LFMR signals emitted by the presence of the desired substance being analyzed (g) calculating the concentration of the substance in the sample being analyzed (h) repeating steps (a) to (g) for the next substance in the sample being analyzed In one exemplary embodiment, the method further includes calibrating the probe for precise calculations of the concentration of the desired substance in the sample being analyzed.

In one exemplary embodiment, the method further includes measuring a temperature in or around the sample to adjust the preset resonant frequency of RF pulses, parameters of RF pulses and receiving parameters.

In one exemplary embodiment, the method further includes applying a sequence of RF pulses (e.g., a pulse sequence) or combination of pulse sequences chosen to correspond to the desired substance to be analyzed.

In one exemplary embodiment, the pulse sequence is of the SE or SLSE type.

In another exemplary embodiment, the pulse sequence may be of the CPMG type.

In yet another exemplary embodiment, the pulse sequence may be of the SSFP type.

In a different exemplary embodiment, the method may include applying single pulses being chosen to correspond to the desired substance to be analyzed.

In various exemplary embodiments, the method further includes processing any received response signals to detect the presence of an NQR and/or LFMR signal corresponding to the desired substance being targeted.

In various exemplary embodiments, the method further includes measuring an intensity and line width of any received NQR or LFMR signals corresponding to the desired substance being analyzed.

In various exemplary embodiments, the method further includes measuring first and second relaxation times T1 and T2 if a signal is received that indicates an NQR or LFMR signal corresponding to the desired substance being analyzed.

In various exemplary embodiments, the method further includes calculating the concentration of each substance containing the same element in the sample being analyzed.

In various exemplary embodiments, the method includes calculating the total concentration of a chemical element in the sample being analyzed.

In various exemplary embodiments of the present invention, the method may include simultaneous detection of NQR or LFMR in more than one substance in the sample being analyzed.

In various exemplary embodiments of the present invention, an apparatus for the mineral analysis and exploration using NQR and/or LFMR detection technique includes a probe, the probe including a tank circuit with a coil system, a tuning and matching circuit, and a Q-factor changing circuit; a transmitter, the transmitter being usable to provide and/or apply RF pulses from an output of the transmitter to the tank circuit; a receiver, the receiver being tunable to at least one channel for detecting and amplifying signals received in the coil system; and a processor for processing the signals amplified by the receiver to help distinguish the presence of any NQR and/or LFMR signals corresponding to a desired substance being targeted within the sample, the processor may also be usable to calculate the concentrations of the substance within the sample.

In various exemplary embodiments, the Q-factor changing circuit is controllable to change a Q-factor of the tank circuit. In various exemplary embodiments, the Q-factor of the tank circuit may be adjusted to a desired level during a prescribed transmitting period of an RF pulse for irradiating the sample with RF energy. In various exemplary embodiments, the Q-factor of the tank circuit may be adjusted to a minimal level during a prescribed recovery period immediately following a transmitting period to rapidly dampen transient signals from the probe.

In various exemplary embodiments, the Q-factor of the tank circuit may be adjusted to a maximal level during a prescribed receiving period for detecting an NQR and/or LFMR signal from the target substance, if present, immediately following the recovery period.

In various exemplary embodiments, the probe may be usable inside a borehole for borehole logging, and the coil system may be designed to be usable for creating an RF field in, and receiving signals from, a sample surrounding the probe.

In various other exemplary embodiments, the probe may be designed to be usable for analyzing a sample when the sample is placed into the probe. Likewise, the coil system may be designed to be usable for creating and RF field and/or receiving signals inside the probe.

In various other exemplary embodiments, the probe may be designed to be usable for analyzing a sample when the sample is placed at a desired distance from the probe. Likewise, the coil system may be designed to be usable for creating an RF field in, and receiving signals from, the sample outside the probe.

In various exemplary embodiments, the apparatus includes measuring circuits and/or sensors for measuring a weight and volume of the sample to be analyzed.

In various exemplary embodiments, the apparatus includes measuring circuits and/or sensors for measuring a distance between the probe and the sample to be analyzed.

In various exemplary embodiments, the probe includes one tank circuit, the tank circuit including a coil system which can be tuned to any desired NQR and/or NMR frequencies of the substances to be analyzed.

In various other exemplary embodiments, the probe may include several tank circuits, each tank circuit including a separate coil systems which can be tuned to different NQR and/or LFMR frequencies of the substances to be analyzed.

In various exemplary embodiments, the coil system includes one coil.

In various other exemplary embodiments, the coil system includes more than one coil.

In various other exemplary embodiments, the probe includes a temperature sensor for measuring the temperature inside and/or around the probe to adjust the preset resonant frequency of RF pulses.

These and other features and advantages of various exemplary embodiments of systems and methods according to this invention are described in, or are apparent from, the following detailed descriptions of various exemplary embodiments of various devices, structures and/or methods according to this invention.

BRIEF DESCRIPTION OF DRAWINGS

Various exemplary embodiments of the systems and methods according to this invention will be described in detail, with reference to the following figures, wherein.

DETAILED DESCRIPTION

In various exemplary embodiments, the present invention is directed toward a method and apparatus for mineral analysis and exploration employing both NQR and NMR phenomena for detecting the presence of and, if present, measuring a concentration of one or more target (e.g., desired) substances containing quadrupolar nuclei and nuclei with a magnetic moment within a sample.

Exemplary embodiments of the present invention will now be described with reference to an apparatus for the mineral analysis and exploration based on using both "pure NQR" and Local Field Magnetic Resonance. However, it should be appreciated that various exemplary embodiment of an apparatus and method according to the present invention may be usable for other purposes. Further, various exemplary embodiments may be advantageous over currently used active nuclear techniques.

Figure 1:
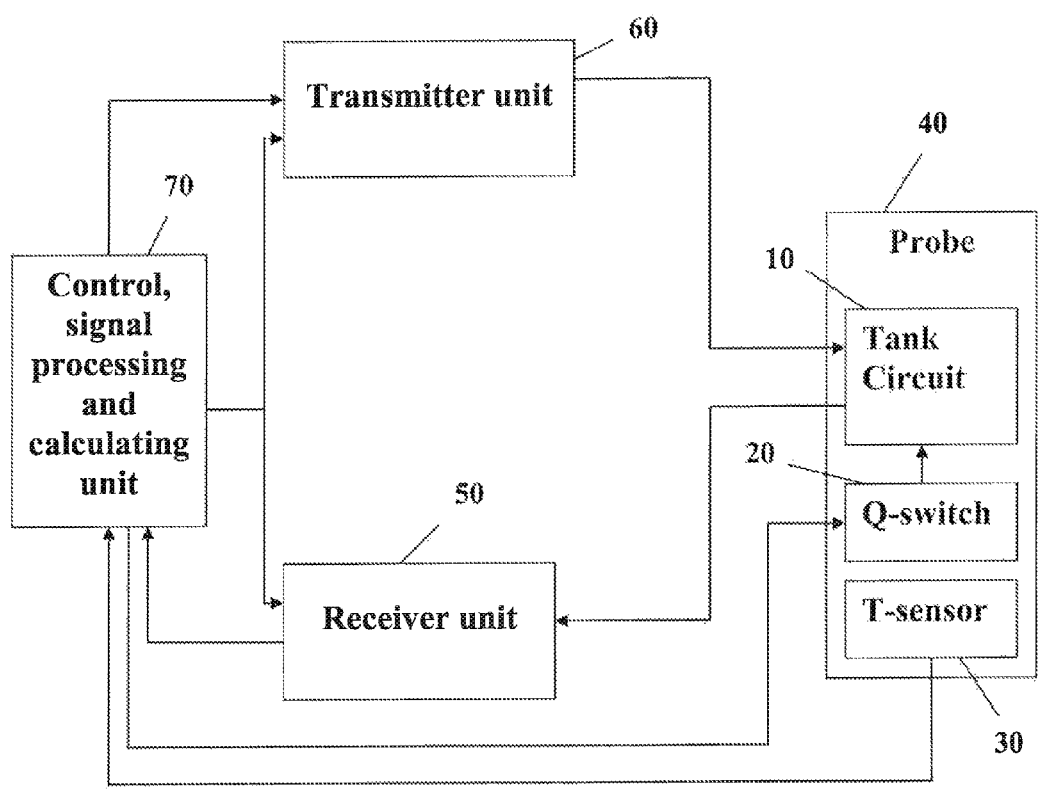
FIG. 1 is a block diagram illustrating an apparatus for mineral analysis and exploration, according to an exemplary embodiment of the present invention.

FIG. 1 is a block diagram illustrating an apparatus for mineral analysis and exploration based on using "pure NQR" and LFMR, according to an exemplary embodiment of the present invention. As shown in FIG. 1, a probe 40 is connected to a receiver unit 50 and a transmitter unit 60. It should be appreciated that the receiver unit 50 and the transmitter unit 60 may be any known or later-developed receiving and transmitting devices (e.g., a conventional receiver and transmitter). The probe 40 includes a tank circuit 10, Q-switch unit 20 and a temperature sensor (T-sensor) 30. The tank circuit 10 may be tuned to a frequency of particular interest. The tank circuit 10 generally includes a coil system, capacitors, tuning circuits and matching circuits. The tank circuit 10 is connected to the receiver unit 50 and the transmitter unit 60.

The transmitter unit 60 generates RF pulses and transfers these pulses to the probe 40 and the tank circuit 10. The pulses are transmitted at a desired power, typically from tens of watts to several hundred watts or even to several kilowatts. These RF pulses can excite NQR or LFMR signals in the sample under investigation that is located within the bounds of the probe 40. This signal is amplified and/or detected by the receiver unit 50 and is then delivered for further mathematical processing into a control, signal processing and calculating unit 70, one of the inputs of which is connected to the output of the receiver unit 50. It should be appreciated that the control, signal processing and calculating unit 70 may be any known or later-developed processor such as, for example, a microprocessor or microcontroller. After mathematical processing, in the control, signal processing and calculating unit 70, the signal is used for further calculating of the substance concentration in the sample being analyzed.

The control, signal processing and calculating unit 70 generates an RF signal, which is transmitted to one of the inputs of the transmitter unit 60 for further formation of the RF carrier for the RF pulses, and to one of the inputs of the receiver unit 50 to act as a reference frequency. The control, signal processing and calculating unit 70 also generates signals to another input of the transmitter unit 60 and prescribes parameters for the RF pulses and the control signals, which are transmitted to the input of the Q-switch unit 20 to change or control the Q-factor of the tank circuit 10.

The Q-factor of the tank circuit 10 may be changed to an first level during a prescribed transmitting period of an RF pulse for irradiating the sample with said RF energy, a second level during a prescribed recovery period immediately following said transmitting period to rapidly dampen transient signals from the probe and/or a third level during a prescribed receiving period for detecting an NQR or LFMR signal from the target substance if present, immediately following the recovery period.

The T-sensor 30 measures the temperature of (or near) a sample being analyzed. The signal generated by T-sensor 30 is delivered into the control, signal processing and calculating unit 70, one of the inputs of which is connected to the output of the T-sensor 30. According to the ambient temperature that is sensed by T-sensor 30, the control, signal processing and calculating unit 70 adjusts the RF carrier to be close to one of the NQR frequencies of the substance which is expected to be in the sample being analyzed.

The control, signal-processing and calculating unit 70 usually consists of a computer, an RF signal source for producing the RF pulses and electronic circuits for producing the control signals.

Various exemplary embodiments of an apparatus and method according to this invention may be particularly effective for the detecting, identifying and/or measuring a concentration of substances containing quadrupolar nuclei and/or nuclei with a magnetic moment. Examples of such substances include, for example, copper minerals such as different sulphides and oxides: $CuS$, $Cu_2S$, $CuFeS_2$, $CuFe_2S_3$, $Cu_3SbS_3$, $Cu_3BiS_3$, $Cu_2O$ and $CuO$. These substances have been investigated, and strong NQR and/or LFMR signals in the local magnetic field have been obtained.

Figure 2:
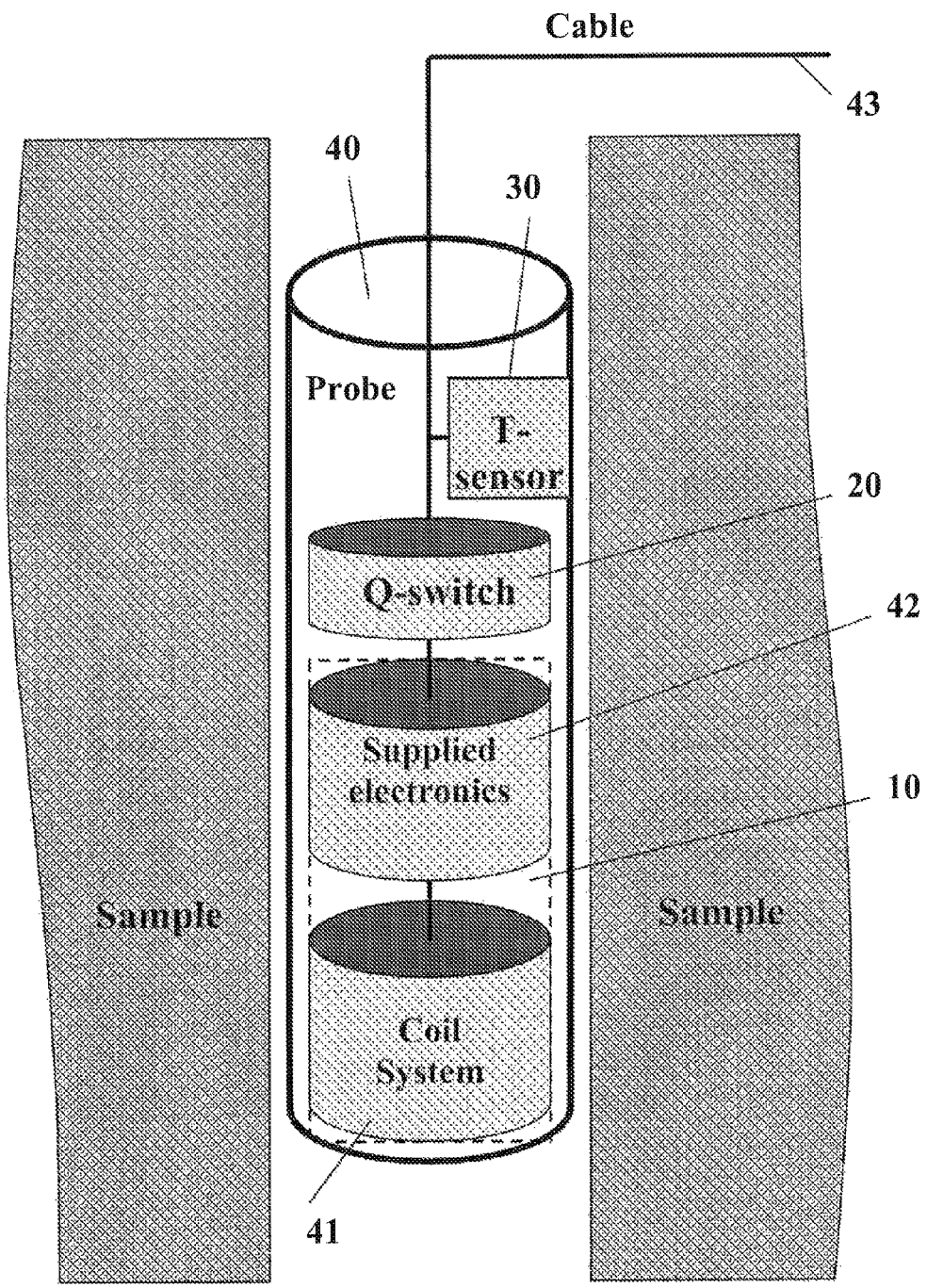
FIG. 2 is a block diagram and borehole configuration of a probe for mineral analysis and exploration, according to an exemplary embodiment of the present invention.

FIG. 2 shows an exemplary embodiment of the invention directed toward an apparatus with an exemplary embodiment of a probe that may be usable to borehole logging in mineral exploration. This exemplary embodiment of the probe may be particularly suitable for use in mining operations, in blastholes and exploration holes, both underground and open-pit configurations.

As shown in FIG. 2 the probe 40, includes a tank circuit 10, Q-switch unit 20 and a temperature sensor (T-sensor) 30. The probe is connected to the receiver unit 50, the transmitter unit 60 and the control, signal processing and calculating unit 70 (shown in FIG. 1) by a cable 43. The tank circuit comprises a coil system 41 and supplied electronics 42 that include matching and tuning circuits for matching and tuning to the predetermined resonance frequency (equal or close to the RF carrier) of the substance to be detected that exhibits NQR properties.

The coil system 41 is configured to provide optimal excitation and detection NQR and/or LFMR signals from the sample surrounding the probe 10 as shown in FIG. 2. It should be appreciated that the coil system 41 may include one, two or several coils. Additionally, each coil of the coil system 41 may be a single turn or multi-turn coil. Further, in various exemplary embodiments, the Q-switch unit 20 and/or the temperature sensor (T-sensor) 30 may be omitted.

Figure 3:
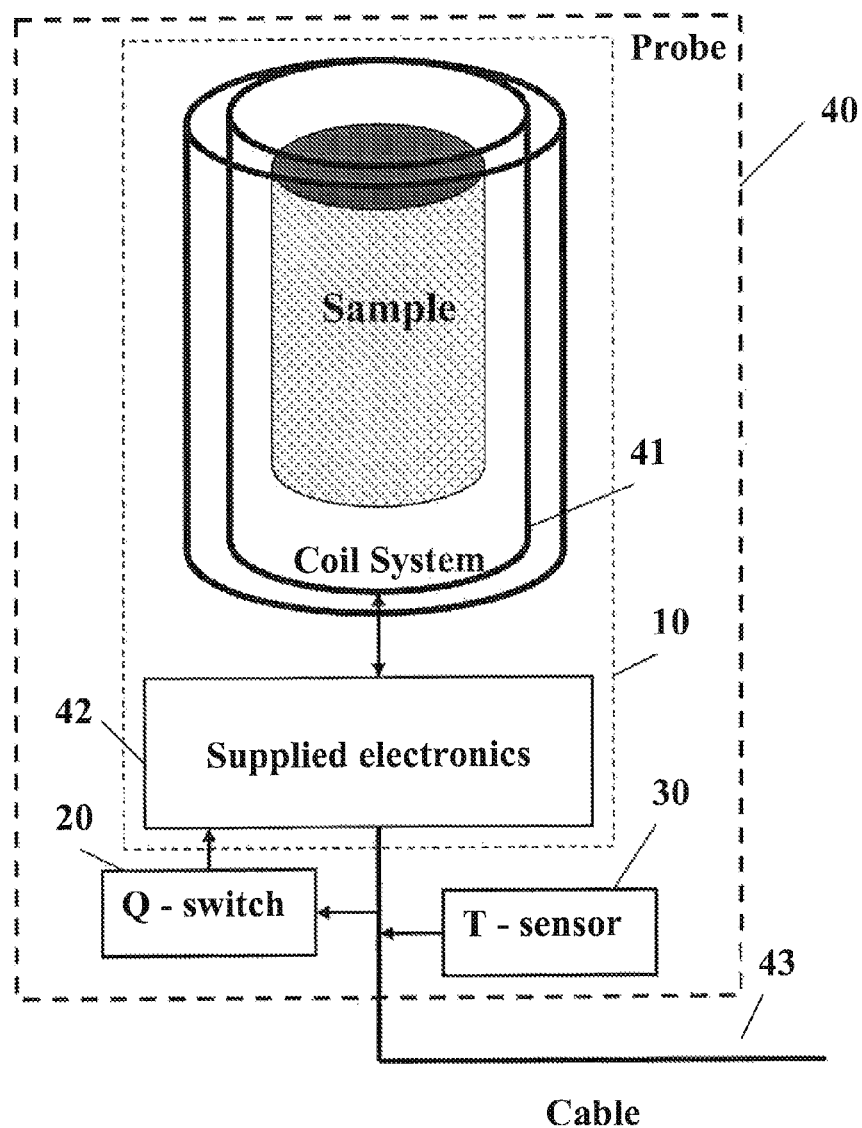
FIG. 3 is a block diagram and volume configuration of a probe for mineral analysis and exploration, according to an exemplary embodiment of the present invention.

FIG. 3 shows another exemplary embodiment according to this invention, including another exemplary embodiment of the probe 40. Similar to the embodiment shown in FIG. 2, the probe 40 includes a tank circuit 10, a Q-switch unit 20 and a temperature sensor (T-sensor) 30. Likewise, the tank circuit includes a coil system 41 and supplied electronics 42 that include matching and tuning circuits.

In contrast to the embodiment shown in FIG. 2, the coil system 41 shown in FIG. 3 is configured to be particularly useful at providing excitation and/or detection of NQR and/or LFMR signals when the sample is placed inside the coil system 41. That is, the coil system 41 is designed for "volume detection" of the sample. It should be appreciated that, in various exemplary embodiments, the coil system 41 may include one, two or several coils. Likewise, each coil of the coil system 41 may be a single turn or multi-turn coil.

It should also be appreciated that the exemplary embodiment shown in FIG. 3 can be used both at a mine site and in the laboratory. Further, in various exemplary embodiments, the Q-switch unit 20 and/or the temperature sensor (T-sensor) 30 may be omitted.

Figure 4:
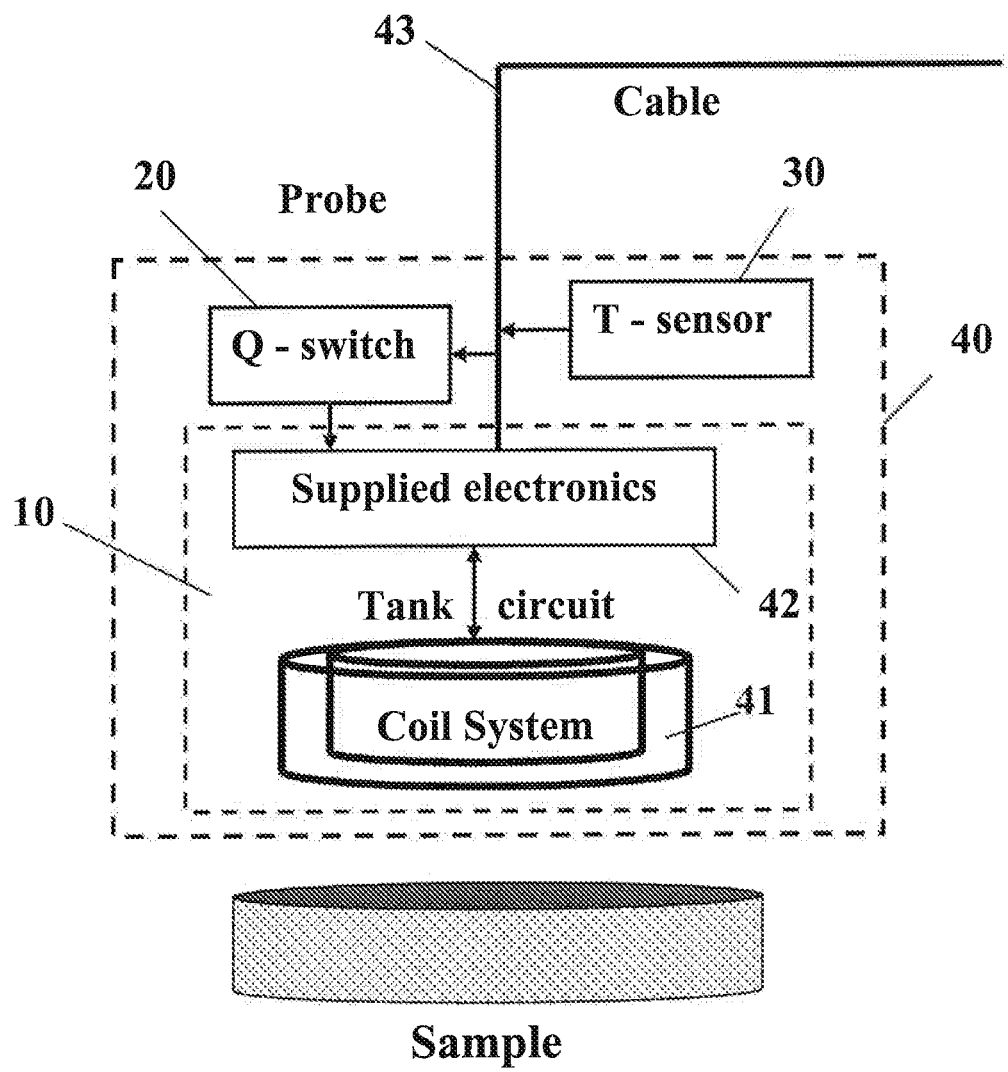
FIG. 4 is a block diagram and surface configuration of a probe for mineral analysis and exploration, according to an exemplary embodiment of the present invention.

FIG. 4 shows yet another exemplary embodiment of a probe 40 according to this invention. The embodiment shown in FIG. 4 is substantially the same as the embodiment shown in FIG. 3, except that the coil system 41 is configured to be particularly useful at providing excitation and detection of NQR and/or LFMR signals from the sample when the sample is placed a distance from the coil system 41. That is, the coil system 41 is designed for "one side or surface detection" of the sample. In this embodiment, the coil system 41 includes at least one surface coil. It should be appreciated that, in various exemplary embodiments, the Q-switch unit 20 and/or the temperature sensor (T-sensor) 30 may be omitted.

Figure 5:
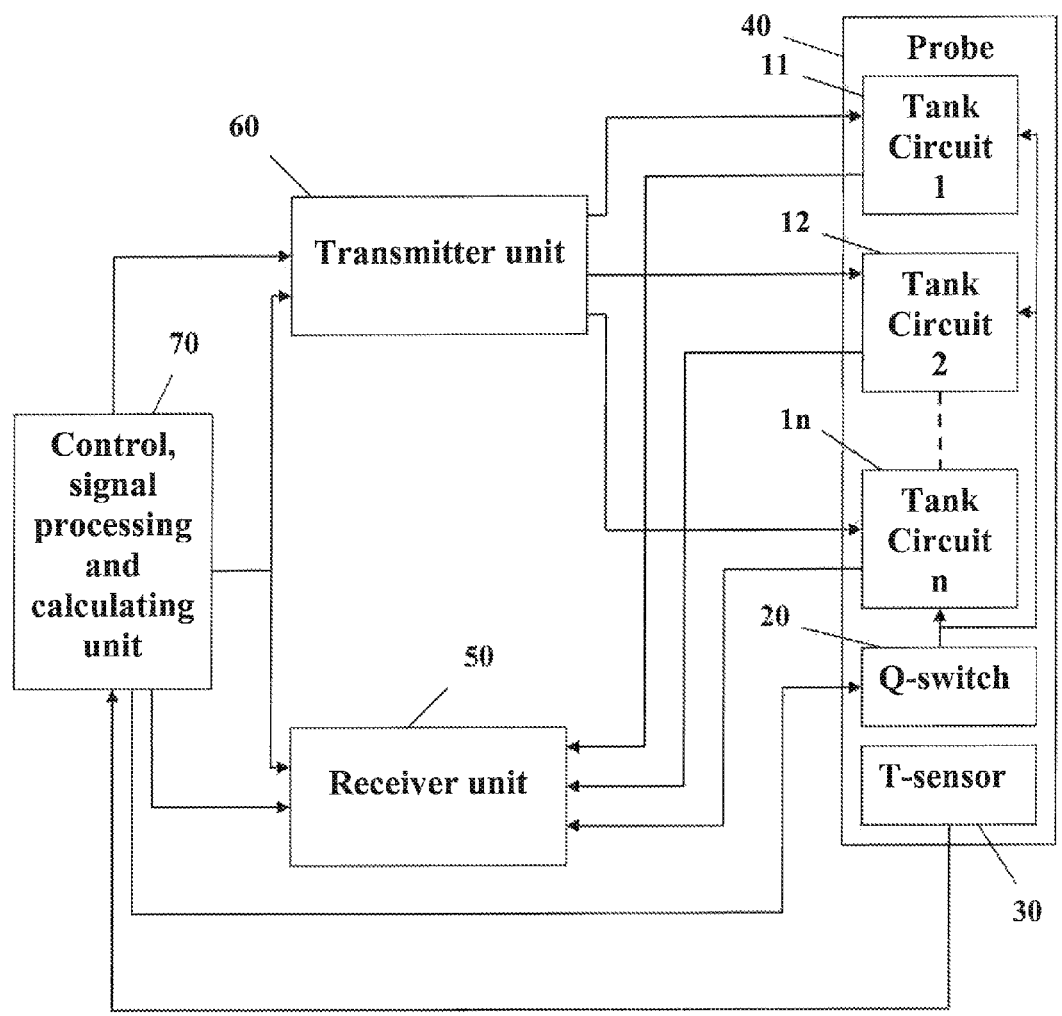
FIG. 5 is a block diagram illustrating an apparatus with a probe including a plurality of tank circuits for mineral analysis and exploration, according to an exemplary embodiment of the present invention

FIG. 5 shows a block diagram illustrating an exemplary embodiment of an improved version of an apparatus for mineral analysis and exploration based on using "pure NQR" and LFMR according to this invention. This embodiment shown in FIG. 5 is very similar to the embodiment shown in FIG. 1, except that the probe 40 comprises several (more than one) tank circuits 11, 12 . . . 1n. Each of the tank circuits is tuned to different NQR or LFMR frequencies (e.g., to frequencies that correspond to different substances). This improved version of apparatus can be used for simultaneous detection of different substances in the sample to be analyzed.

This improved version of the apparatus may include any version of the probe 10 described above with regard to FIGS. 2-4.

It should be appreciated that the scope of the present invention is not limited to the particular embodiments described herein, and that minor changes or variations to the elements may be made that do not depart from the spirit of the invention and thus remain within its scope.

It should also be appreciated that although the embodiments have been specifically described for direct application using NQR techniques, these embodiments are just as easily applied to LFMR using NQR techniques.

A method for the mineral analysis of a sample containing substances with nuclei responsive to the Nuclear Quadrupole Resonance (NQR) and/or Local Field Magnetic Resonance (LFMR) phenomenon, which comprises exciting, and detecting NQR and/or LFMR signals from a particular substance that is targeted within the sample, measuring the intensity of any detected signal, and calculating the concentration of the substance in the sample being analyzed.

A method as in the preceding paragraph, and comprising the following steps:

(a) setting a frequency of the radio-frequency (RF) pulses to be equal or near to one of the NQR or LFMR frequencies of the substance to be analyzed; and (b) setting all parameters of the RF pulses: amplitude, phase, duration, shape, number and repetition time or time between pulses to be optimal for the substance to be analyzed; and (c) setting all receiving parameters including (but not limited) the gain, reference phase, acquisition time and acquisition number to be optimal for the substance to be analyzed; and (d) transmitting the RF pulses at optimal level during the prescribed transmitting period to irradiate the sample and excite an NQR or LFMR signal in the sample if a substance providing for NQR or LFMR is present; and (e) detecting and processing NQR or LFMR signals emitted by the substance being analyzed; and (f) measuring the intensity of NQR or LFMR signals emitted by the substance being analyzed; and (g) calculating the concentration of the substance in the sample being analyzed; and (h) repeating steps (a) to (g) for the next substance in the sample being analyzed.

The method may further include calibrating the probe for precise calculations of the concentration of the substance in the sample being analyzed.

The method may further include measuring a temperature of or around the sample to adjust the preset resonant frequency of RF pulses, parameters of the RF pulses and receiving parameters.

A method as in any of the preceding paragraphs, comprising simultaneous detection NQR or LFMR in more than one substance in the sample being analyzed.

A method as in any of the preceding paragraphs, comprising processing any received response signals to detect the presence of an NQR or LFMR signal corresponding to a substance being targeted.

A method as in the preceding paragraph, comprising measuring an intensity and line width of received an NQR or LFMR signal corresponding to a substance being analyzed.

A method as in the preceding paragraph, comprising measuring relaxation times T1 and T2 if received signal is an NQR or LFMR signal corresponding to a substance being analyzed.

A method as in any the preceding paragraph, comprising calculating the total concentration of the chemical element in the sample being analyzed.

A method as in the preceding paragraph, comprising applying a sequence of RF pulses (pulse sequence) or combination of pulse sequences being applicable and optimal for the substance to be analyzed.

The method may further include the pulse sequence being of the SE or SLSE type.

Alternatively, the pulse sequence may be of the CPMG type.

Likewise, the pulse sequence may be of the SSFP type.

A method as in any of the preceding paragraphs, further comprising applying a single RF pulse being applicable and optimal for the substance to be analyzed.

An apparatus for the mineral analysis of the sample containing substances with nuclei responsive to the Nuclear Quadrupole Resonance (NQR) and/or Local Field Magnetic Resonance (LFMR) phenomenon, comprising:
a probe comprising a tank circuit with a coil system, tuning and matching means, and;
transmitting means for providing and applying powerful RF pulses at the output thereof to the tank circuit; and
receiving means comprising at least one channel for detecting and amplifying signals received in the coil system; and
processing and calculating means for processing the signals amplified by said receiving means to distinguish the presence of any NQR or LFMR signals corresponding to a substance being targeted within the sample and calculating the concentrations of said substance within the sample; and
calibrating means for precise calculations of the concentration of the substance in the sample being analyzed comprising at least one sample containing the substance with nuclei responsive to the Nuclear Quadrupole Resonance (NQR) and/or Local Field Magnetic Resonance (LFMR) the concentration of said substance in the sample is well known.

An apparatus as in the preceding paragraph, including Q-factor changing means, wherein the Q-factor changing means is controllable to change the Q-factor of the tank circuit to:
an optimal level during a prescribed transmitting period of an RF pulse for irradiating the sample with said RF energy;

a minimal level during a prescribed recovery period immediately following said transmitting period to rapidly dampen transient signals from the probe; and a maximal level during a prescribed receiving period for detecting an NQR or LFMR signal from the target substance if present, immediately following the recovery period.

An apparatus as in any of the preceding paragraphs, wherein the said probe comprises several tank circuits each of them is tuned to different frequency according to NQR or LFMR frequencies of the substances to be analyzed.

An apparatus as in any of the preceding paragraphs, wherein the said probe comprises at least one temperature sensor.

An apparatus as in any of the preceding paragraphs, wherein the said coil system comprises one coil.

An apparatus as in any of the preceding paragraphs, wherein the said coil system comprises more than one coil.

An apparatus as the preceding two paragraphs, wherein the said probe designed to be used inside a borehole for borehole logging, and the said coil system is designed to be optimal for creating RF field in and receiving signals from the sample surrounding the probe.

An apparatus as in any of the preceding paragraphs, wherein the said probe designed for the sample analysis there the said sample is placed into the probe, and the coil system is designed to be optimal for creating RF field and receiving signals inside the probe.

An apparatus as in any of the preceding paragraphs, wherein the said probe designed for the sample analysis there the said sample is placed at the some distance from the probe, and the coil system is designed for one side detection to be optimal for creating RF field in and receiving signals from the sample outside the probe.

An apparatus as in the preceding two paragraphs, comprising measuring means for measuring a weight and volume of the sample to be analyzed.

An apparatus as in the preceding three paragraphs, comprises measuring means for measuring a distance between the probe and the sample to be analyzed.

Method and apparatus for the mineral analysis of the sample based on detection NQR and/or LFMR signals from a particular substance that is targeted within a sample are disclosed. The method comprises following steps:

(a) setting a frequency of the RF pulses to be equal or near to one of the nuclear quadrupole resonance or nuclear magnetic resonance frequencies of the substance to be analyzed;
(b) setting all parameters of the RF pulses: amplitude, phase, duration, shape, number and repetition time or time between pulses to be optimal for the substance to be analyzed;
(c) setting all receiving parameters including (but not limited) the gain, reference phase, acquisition time and acquisition number to be optimal for the substance to be analyzed;
(d) tuning the probe to maximum sensitivity for the signals detected at predetermined frequency and/or to maximum power transfer efficiency for RF pulses transmitted with the probe;
(e) transmitting the RF pulses with the probe at said optimal level during the prescribed transmitting period to irradiate the sample and excite an NQR or LFMR signal in the sample if a substance providing for NQR or LFMR is present;
(f) detecting and processing NQR or LFMR signals emitted by the substance being analyzed
(g) calculating the concentration of the substance in the sample being analyzed
(h) repeating steps (a) to (g) for the next substance in the sample being analyzed.

The said method of the invention has particular application to (but not limited to) the mine site exploration and ore delineation including the bore-hole logging of ore formations.

What is claimed is:

1. An apparatus usable for mineral analysis of a sample containing at least one substance with nuclei responsive to a Nuclear Quadrupole Resonance (NQR) and/or Local Field Magnetic Resonance (LFMR) phenomenon, comprising:

a probe comprising a tank circuit with a coil system, tuning, and matching means;
transmitting means usable to provide and apply powerful radio-frequency (RF) pulses at an output thereof to the tank circuit;
receiving means comprising at least one channel for detecting and amplifying signals received in the coil system;
processing and determining means usable to process the signals amplified by said receiving means to help distinguish the presence of any NQR or LFMR signals corresponding to a substance being targeted within the sample and determining a concentration of the substance being targeted within the sample; and
calibrating means usable to improve determinations of the concentration of the substance being targeted in the sample being analyzed, the calibrating means comprising at least one test sample containing a test substance with nuclei responsive to the Nuclear Quadrupole Resonance (NQR) and/or Local Field Magnetic Resonance (LFMR) in local magnetic field, the concentration of the test substance in the test sample being well known.

2. The apparatus of claim 1, further comprising Q-factor changing means, wherein the Q-factor changing means is controllable to change a Q-factor of the tank circuit to:

an optimal level during a predetermined transmitting period of an RF pulse for irradiating the sample with RF energy;
a minimal level during a predetermined recovery period immediately following said transmitting period to rapidly dampen transient signals from the probe; and
a maximal level during a predetermined receiving period for detecting an NQR or LFMR signal from the substance being targeted immediately following the recovery period.

3. The apparatus of claim 1, wherein the probe comprises several tank circuits each being tuned to different frequencies corresponding to NQR or LFMR frequencies of several substances to be analyzed.

4. The apparatus of claim 1, wherein the probe comprises at least one temperature sensor.

5. The apparatus of claim 1, wherein the coil system comprises at least one coil.

6. The apparatus of claim 1, wherein the probe is adapted to be usable inside a borehole for borehole logging, and the coil system is adapted to be optimal for creating RF field in and receiving signals from the sample surrounding the probe.

7. The apparatus of claim 1, wherein the probe is adapted for sample analysis with the sample placed within a housing of the probe, and the coil system is adapted to be optimal for creating an RF field and receiving signals within the housing of the probe.

8. The apparatus of claim 7, further comprising measuring means for measuring at least one of a weight and a volume of the sample to be analyzed.

9. The apparatus of claim 1, wherein the probe is adapted for sample analysis with the sample provided at a distance from the probe, and the coil system is adapted for one side detection to be optimal for creating RF field in and receiving signals from the sample outside the probe.

10. The apparatus of claim 9, further comprising measuring means for measuring a distance between the probe and the sample to be analyzed.

\* \* \* \* \*